United States Patent [19]

Daiss

[11] Patent Number: 4,950,592
[45] Date of Patent: Aug. 21, 1990

[54] BLEND OF MONOCLONAL ANTIBODIES

[75] Inventor: John L. Daiss, Rochester, N.Y.

[73] Assignee: Eastman Kodak Company, Rochester, N.Y.

[21] Appl. No.: 48,847

[22] Filed: May 12, 1987

[51] Int. Cl.$^5$ .................... G01N 33/53; C12Q 1/48
[52] U.S. Cl. .......................................... 435/7; 435/17; 435/172.2; 435/240.27; 530/387; 935/103; 935/110; 436/548
[58] Field of Search ............ 435/7, 17, 172.2, 240.27; 530/808, 809, 387; 935/103, 110; 436/548

[56] References Cited

U.S. PATENT DOCUMENTS 4,067,775  1/1978  Wurzburg et al. .................. 195/99

OTHER PUBLICATIONS

Sevier et al., Monoclonal Antibodies in Clinical Immunology, Nov. 1981, Clin. Chem., 1797–1806.
Morris et al., Biochem. J., vol. 228, No. 2, pp. 375–381, 1985, Monoclonal–Antibody Studies of Creatine Kinase.
Jackson et al., Biochem. Soc. Trans., vol. 13, No. 1, pp. 99–100, 1985, Monoclonal Antibodies Against Creatine Kinase Isoenzymes.
Clin. Chem., Piran et al., vol. 33, No. 9, pp. 1517–1520, 1987.
Paul, Fundamental Immunology, published by Raven Press, 1984, pp. 762 and 764.
Paul, Fundamental Immunology, Published by Raven Press, 1984, pp. 759–760.

*Primary Examiner*—Esther M. Kepplinger
*Assistant Examiner*—Laurie A. Scheiner
*Attorney, Agent, or Firm*—John R. Everett

[57] ABSTRACT

A blend of monoclonal antibodies is disclosed. The blend inhibits the activity of creatine kinase-MM at least 99.5 percent. The blend is useful in determining the level of creatine kinase-MB activity in biological fluids.

9 Claims, 2 Drawing Sheets

BLEND OF MONOCLONAL ANTIBODIES

FIELD OF THE INVENTION

This invention relates to a blend of antibodies, the specific antibodies of the blend, the hybridomas secreting the antibodies and the use of the blend in assaying the catalytic activity of creatine kinase-MB in aqueous biological fluids.

BACKGROUND OF THE INVENTION

The determination of the activity of Creatine Kinase (ATP: creatine-phosphotransferase, E.C. 2.7.3.2; abbreviation; CK) in human serum is considered the most sensitive laboratory method for diagnosing diseases of skeletal muscle and myocardial infarction. However, differentiation between trauma of skeletal muscles and the myocardium is difficult, especially in making a differential diagnosis of myocardial infarction. Determination of total CK activity results in unreliable differentiation.

CK occurs in the body in the form of three isoenzymes; creatine kinase-MM in muscles; creatine kinase-BB in the brain; and hybrid creatine kinase-MB, consisting of an M and a B-subunit in the myocardium. CK activity in blood serum is normally due to the creating kinase-MM isoenzyme, because creating kinase-BB does not turn over rapidly and creatine kinase-MB is restricted to certain organs, for example, the myocardium. However, when the myocardium is damaged, as in cardiac infarction, creatine kinase-MB is released into the blood serum and can be detected there.

Quantitative determination of creatine kinase-MB and creatine kinase-MM in the serum is considered the most sensitive laboratory method and provides the greatest evidence in differential diagnosis of cardiac infarction. It is true that creatine kinase-MB is present in other organs, for example, the pancreas, the diaphragm, the aorta, the lungs and the uterus, as well as in the myocardium but the activity thereof in these organs is about 100 times less than in the myocardium, so that any creatine kinase-MB activity liberated from these other organs is below the limits of detection.

U.S. Pat. No. 4,067,775 discloses a method for determining the enzymatic activity of creatine kinase-MB is a biological sample. The method involves:

(a) incubating the creatine kinase-containing sample with polyclonal antibodies which inhibit the enzymatic activity of the M-subunit of creatine kinase (CK) isoenzymes MB and MM; and (b) determining the enzymatic activity of the creatine kinase B-subunit after inhibition of the M-subunit.

The level of creatine kinase-MM normally in human blood is about 25 to 100 times greater than creatine kinase-MB and about 1,000 times greater than creatine kinase-BB. Any assay for creating kinase-MB must therefore be extremely sensitive. At least 99.5 percent of the creatine kinase-MM activity must be suppressed. Otherwise the activity of creatine kinase-MB will be completely masked. The polyclonal antibodies of the above prior art do not necessarily provide the desired level of creatine kinase-MM inhibition. Moreover, polyclonal antibodies suffer from lot-to-lot variation and the inhibition of creatine kinase-MB activity is so high (typically greater than 60 percent) that the sensitivity of the assay is reduced.

SUMMARY OF THE INVENTION

The present invention provides a blend of monoclonal antibodies comprising:

(a) a first monoclonal antibody which
  (i) inhibits the activity of creatine kinase-MM 55 to 65 percent;
  (ii) is not an inhibitor of the catalytic activity of creatine kinase-MB; and
  (iii) binds only to creatine kinase-MM;

(b) a second monoclonal antibody which
  (i) inhibits the catalytic activity of creatine kinase-MM 85 to 95 percent;
  (ii) inhibits the catalytic activity of creatine kinase-MB 35 to 45 percent; and
  (iii) binds creatine kinase-MM and creatine kinase-MB equally; and (c) a third monoclonal antibody which
  (i) inhibits the catalytic activity of creatine kinase-MM 85 to 95 percent;
  (ii) inhibits the catalytic activity of creatine kinase-MB 35 to 45 percent; and
  (iii) has greater binding strength to creatine kinase-MM than to creatine kinase-MB.

The monoclonal antibody blend of this invention inhibits the catalytic activity of creatine kinase-MM at least 99.5 percent and creatine kinase-MB about 40 percent. Each of the different antibodies in the blend is secreted by a different hybridoma cell. The characteristic of each of the different antibodies is therefore uniform. Hence, the antibodies and the blends made therefrom do not suffer lot-to-lot variations that create uncertainty. Since the antibodies are produced by hybridomas, an unliminted supply of the antibodies is always available.

Thus the present invention also provides three different hybridoma cells as follows:

(1) a hybrodoma cell which
  (a) is formed by fusing mouse myeloma cells with rate spleen cells;
  (b) secretes monoclonal antibodies which inhibit the catalytic activity of creatine kinase-MM from 85 to 95 percent; and inhibits the catalytic activity of creatine kinase-MB from 35 to 45 percent.

(2) a hybridoma cell which
  (a) is formed by fusing mouse myeloma cells with rate spleen cells;
  (b) secretes monoclonal antibodies which inhibit the activity of creatine kinase-MM from 55 to 65 percent; and are not inhibitors of the activity of creatine kinase-MB; and (3) a hybridoma cell which
  (a) is formed by fusing mouse myeloma cells with rat spleen cells; and
  (b) which secretes monoclonal antibodies which inhibit the catalytic activity of
    (i) creatine kinase-MM 85 to 95 percent;
    (ii) creatine kinase-MB 35 to 45 percent; and
    (iii) has greater binding strength to creatine kinase-MM than creatine kinase-MB.

DETAILS OF THE INVENTION

Figure 1:
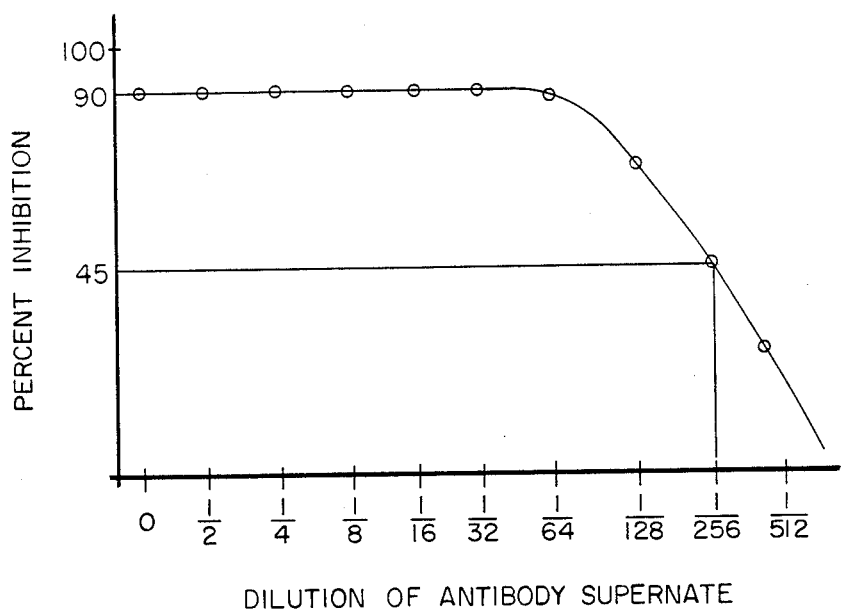
FIG. 1 describes the method for determining inhibition units in antibody supernate.
Figure 2:
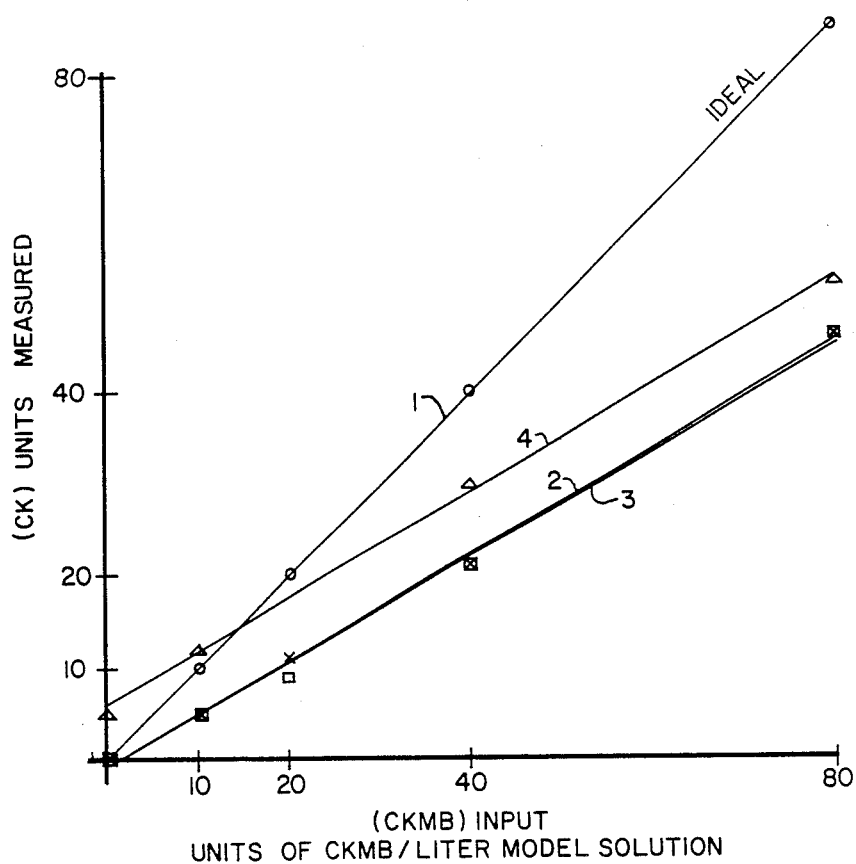
FIG. 2 describes a series of inhibition assays using a blend of this invention.

Each of the monoclonal antibodies used in the blend of antibodies of this invention were made in a process having several general steps. The steps are identification of the desired immunogens; immunization and screening to obtain the desired antibodies; fusion of selected myeloma cells with selected spleen cells to make a hybridoma capable of producing the desired monoclonal antibodies; screening to identify the desired hybridomas and cloning, screening and recloning the hybridomas as needed for perpetual production of the antibodies.

Step 1 Identification of Immunogen

The general choice of immunogen is established by the use to which the antibodies are to be put. The immunogen should be as pure as possible. One objective of the present invention is to produce antibodies which will completely inhibit the activity of the M-subunit of creatine kinase. Thus, it is preferable that the immunogen be creatine kinase-MM, free of creating kinase-MB and creatine kinase-BB activities. Criteria by which purity can be assessed include staining for enzymatic activity in agarose gel electrophoresis. Also, analytical isoelectric focusing and polyacrylamide gel electrophoresis are useful. One method of freeing creatine kinase-MM from creating kinase-MB and creating kinase-BB is described by Donald W. Mercer in *Clinical Chemistry*, 20:36–40 (1974). Human creating kinase-MM (h CK-MM) is the preferred immunogen in the present invention.

Human Creatine Kinase-MM (E.C. #2.7.3.2, hCK-MM), purified from skeletal muscle by Aalto Scientific Ltd. was selected as the immunogen herein. Its purity was assessed by SDS-Poly acrylamide gel electrophoresis (SDS-PAGE), isoelectric focusing (IEF) and staining for enzyme activity after electrophoresis in agarose. The immunogen was freed of any creatine kinase-MB and creatine kinase-BB activity. Methods for accomplishing this are disclosed in detail in U.S. Pat. Nos. 4,067,665 and 4,237,044. The purified human creatine kinase-MM was stored at 2°–8° C. in 5 mM tris-succinate buffer, pH 7.0, containing 1 mM disodium ethylenediamine tetraacetic acid (EDTA), 1 mM 2-mercaptoethanol (2-ME) and 10 mM sodium chloride (NaCl). The concentration of the purified enzyme was 5–6 mg/ml and its specific activity was 1100–1150 international units (IU)/mg.

Step 2 Immunization

Immunization is the step in which selected animals are innoculated with the human creatine kinase-MM immunogen thereby eliciting the production of antigen-reactive antibodies from selected B-cells. This step involves several considerations including the type of animal to be used; route of administration of the immunogen to the animal; adjuvant, if any, to be used with the immunogen; quantity of immunogen to be used and the time schedule over which the immunogen is to be administered.

The immunogen can be administered to the selected animal by injection intraperitonelly cavity, intra-muscularly, subcutaneously, intradermally, intrasplenically, etc. In this case, injection into the peritoneal cavity was selected as the route of administration.

It is customary to inject the immunogen in combination with an adjuvant. The purpose of the adjuvant is to assist in sensitizing as many immuno-competent cells, such as B-lymphocytes, as possible. Such sensitization makes the immunogen more effective in eliciting an antibody response in the selected animal.

The choice of adjuvant is dictated by experience and common practice. The most commonly used adjuvant is Freund's Adjuvant (CFA) which was used in the present case. CFA is mineral oil with dead mycrobacteria.

The dosage of immunogen used is subject to wide variations dependent upon the particular animal used, the selected immunogen, availability of the immunogen and the experience of the experimenter with the foregoing variables. In mice, a dosage of 10 to 100 micrograms is widely used. For rats, 50 to 250 micrograms per animal is usual.

The schedule in which the immunogen is administered to the selected animal is also subject to wide variations depending upon many of the same factors mentioned in the immediately preceding paragraph. In the present case monthly administrations were used.

The animals in which the immunogen is injected are selected according to their ability to provide the desired antibody response and according to the level of concentration of the desired antibodies which they are able to produce. To determine this, several different animal types are immunized. For example, different strains of mice and/or different strains of rats are immunized. Periodic assays of the blood of the immunized animal are carried out. Two different assays are used for this purpose.

One assay determines the concentration of antibody in the serum that binds with the immunogen. An example of this assay is the ELISA method. The second assay determines the level of inhibition of an enzyme caused by antibodies in the animal serum. Based on these assays optimal animal choices can be made. Both assays are described hereafter under "Screening Procedures".

Sprague-Dawley rats and mice of three distinct major histocompatibility complex (MHC) haplotypes (Balb/c, A/J and C3H) were immunized herein. Typically, mice received a primary intraperitoneal immunization consisting of 50 $\mu$g human creatine kinase-MM in 200 $\mu$l of Complete Freund's Adjuvant (CFA). Rats received 135 $\mu$g in 500 $\mu$l CFA. Secondary immunizations were administered at 4 to 5 week intervals. Mice were given 20 $\mu$g human creatine kinase-MM intra-peritoneally in 200 $\mu$l Incomplete Freund's Adjuvant (IFA). Rats were given 83 $\mu$g in 0.5 ml IFA.

Seven days following each immunization the animals were bled (rats from the tail; mice from the retroorbital sinus). Serum was prepared from the blood of each animal using standard techniques. A sample of the serum of each animal was introduced into an identified well of a microtiter plate. Portions of each cell were analyzed for antibodies specific for human creatine kinase-MM by the ELISA binding test and the enzyme inhibition test described in detail hereinafter under "Screening Procedures".

Step 3—Preparation of Hybridomas (Fusion) and Screening

This step involves making hybridomas and then screening the hybridomas to identify those which produce monoclonal antibodies which are specific to creatine kinase-MM.

First, spleens of the selected immunized animals are removed. A suspension of the cells of the spleen is made in an appropriate medium. This is accomplished as follows. About one month after the last injection of immunogen is given to the animal, another injection is given. Three to four days later, the animal is sacrificed and its spleen removed. Experience has shown that three to four days after the latter injection, antigen-specific B-cells are present in abundance in the spleen. After preparation of the spleen, the spleen cells are fused with selected myeloma cells. The myeloma cells selected should not produce antibodies. Among the various fusion techniques are chemical fusion and electrofusion. Chemical fusion was used herein.

The fusion process is very inefficient. A mixture of $10^8$ spleen cells with $10^8$ myeloma cells will typically result in $10^4$ hybridomas. Not all of these hybridomas produce the desired antibodies. To select those hybridomas that are producing the desired antibodies, the binding (ELISA) and inhibition assays referred to previously are used.

Hybridomas were also screened for antibody isotypes produced. Although hybridomas may be producing antibodies that are effective in inhibiting CK activity or bind with CK they may be of an isotype that are inconvenient to work with. Herein antibodies of the IgA and the IgG class were selected. However, it should be understood that antibodies of classes such as IgM and IgE having the properties of the desired monoclonal antibodies could be produced by the procedure described herein and are therefore considered within the scope of the present invention.

Antibodies were also screened for cross-reactivity. Since one objective is to make antibodies that are specific for the M-subunit of creatine kinase, those hybridomas that react with the B-subunit are desirably screened out. The ELISA binding assay and the enzyme inhibition are useful in this regard.

Specifically the hybridomas of this invention were prepared as follows.

Animals exhibiting high titers of anti-human creatine kinase-MM antibodies were sacrificed by cervical dislocation (mice) or exsanguination (rats). Their spleens were removed aseptically. After removal of associated fatty tissue, the spleens were dispersed through stainless steel wire mesh screens to yield single cell suspensions in Dulbecco's Modified Eagle's Medium with high glucose (DMEM) supplemented with 10 percent (v/v) Fetal Bovine Serum (FBS). The spleen cells were collected by centrifugation (200 g, 5 minutes) and resuspended in 5 to 10 ml ACK Lysing Buffer (155 mM ammonium chloride, 10 mM potassium bicarbonate, 0.1 mM EDTA, pH 7.2) in order to lyse red blood cells. After a 5 minute incubation at room temperature (RT) 40 ml DMEM was added to the cell suspension and the cells were again collected by centrifugation and resuspended in DMEM. Extracellular protein was removed from the spleen cells by washing them twice by cycles of centrifugation and resuspension in DMEM. The resulting cell suspension was then examined for the concentration of cells (hemocytometer counting) and viability (Trypan Blue exlusion). Typically, these suspensions were about $10^7$ cells/ml and greater than 95 percent viable.

SP2/O-Ag14 (SP2) myeloma cells (Shulman et al, Nature 276, 269, 1978) were cultivated in DMEM supplemented with 10 percent FBS (DMEM-10% FBS) in bottle-necked T-flasks in a standard cell culture incubator (dark, 37° C., 5% $CO_2$ in air, 100% relative humidity). They were split daily each of the four days preceding the fusion to ensure a high percentage of rapidly dividing cells. The SP2 cells were removed from their flasks and collected by centrifugation. They were then washed twice is DMEM and their number and viability determined as previously described herein. Typically, SP2 cells would be concentrated to $5 \times 10^7$ cells/ml and 80 to 95% would be viable.

The spleens cells were then mixed with one-fifth their number of SP2 cells and centrifuged into a common pellet in a $16 \times 125$ round-bottomed polystyrene culture tube. The supernate was then carefully removed and the cell pellet was dispersed by vigorous tapping of the tube. 300 to 400 $\mu l$ of 50% polyethyeneglycol 1500 (PEG) and 10% Dimethyl Sulfoxide (DMSO) in Phsophate-Buffered Saline were then added and the cells were mixed with the PEG-DMSO-PBS by gentle tapping of the tube. After one minute the tube was placed in a centrifuge and spun for 6 minutes (200 g). Exactly 8 minutes after the PEG-DMSO-PBS was added, the supernate was removed and 10 ml DMEM-10% FBS was added. The cells were then gently resuspended and incubated under standard cell culture conditions for one hour. The cells were then collected by centrifugation and resuspended in HAT medium (DMEM supplemented with 20% FBS, 10% v/v NCTC109 from Microbiological Associates, Walkersville, Md., 1 mM oxaloacetic acid, 0.45 mM pyruvic acid, 0.2 u/ml insulin, 0.1 mM hypoxanthine, 0.016 thymidine and 0.4 $\mu M$ aminopterin) at a concentration of $1.6 \times 10^6$ spleen cells/ml. The resulting cell suspension was then distributed into 96-well microculture plates (100 $\mu l$ per well).

The newly formed hybridomas were cultivated under standard conditions with the addition of 100 $\mu l$ HAT medium at roughly weekly intervals. After 11 to 15 days macroscopic colonies of hybridoma cells were apparent in most wells. The hybridomas were then screened to select those making the desired antibodies relative to inhibition, binding, isotype and cross-reactivity described hereinabove using the following screening tests.

Screening

The below described screening tests were used to confirm that desired antibodies for human creatine kinase-MM were actually produced from the immunized animals and to screen out hybridomas that did not produce the desired antibodies during fusing described above and cloning and sub-cloning procedures described hereinafter.

150–200 $\mu l$ of antibody-containing culture supernate was collected from every well of each microtiter plate and apportioned into two other non-sterile microtiter plates as described in the following tests.

(a) Standard ELISA Binding Test

Polystyrene microtiter plates were coated by placing 50 to 100 $\mu l$ of purified human creatine kinase-MM (2 $\mu l$/ml in PBS) in each well and allowing the creatine kinase-MM to adsorb to the plastic surface at room temperature for 2 to 16 hours. PBS is phosphate buffered saline (Dulbecco and Vogt, 1954, J. Exp. Med. 99,167). The plates were then washed 3 times with 300 ml Wash Buffer (PBS with 0.05% Tween-20 and 0.01% merthiolate). Residual polystyrene surface was then "mopped" by adding 200 $\mu l$ of BSA or ovalbumin (1% v/v in PBS) for 2 to 16 hours and then washing 5 times with Wash Buffer. BSA is Bovine Serum Aluminum.

Coated plates were then sealed with adhesive plate sealers and stored at −20° C.

Samples to be screened were added to a human creatine kinase-MM coated microtiter plate (50 to 100 μl/well) and incubated at room temperature for 1 to 2 hours. The plates were washed 5 times with wash buffer and then 100 μl of a dilute solution of horseradish peroxidase-conjugated goat anti-rat (mouse) Ig-Fab$_2$ (HRP-GAR) was added (about 200 mg/ml). The plates were again incubated at room temperature for 1 to 2 hours and washed 5 times with Wash Buffer.

Substrate buffer containing a chromogenic peroxidase substrate was added (50 to 100 μl/well). The immobilized HRP-GAR was allowed to consume the substrate for 10 to 30 minutes (thereby generating color). The reaction was then stopped by the addition of 50 to 100 μl of 4.5M $H_2SO_4$ per well.

The HRP-GAR activity (and therefore the anti-creatine kinase-MM activity) in each well was then determined either by visual inspection or by reading the absorbance on a microtiter plate reader with a 492 nm filter. Those wells scoring about 5 times the control value were selected as positive for containing the desired antibodies.

(b) Enzyme Inhibition Assay

This assay was used to measure the ability of a given monoclonal antibody to inhibit the enzymatic activity of creatine kinase-MM. Each culture supernate (25 μl) was added to a microtiter well of an untreated plate. Then 25 μl of a solution of human creatine kinase-MM (200 U/L in PBS-BSA) was added to each well. After mixing and 10 to 15 minutes incubation at room temperature, 150 μl of CK-NAC (Boehringer-Mannheim's substrate for creatine kinase) was added. The plates were then shaken to ensure good mixing. After brief centrifugation (200 g, 20 seconds) the plates were examined for human creatine kinase-MM activity on a modified microplate reader with a 340 nm filter. Those wells showing reduction (>20%) of human creatine kinase-MM activity compared to an uninhibited control were considered positive.

(c) Screening for Cross-Reactivity of Antibodies

Cultures which scored positive for anti-human creatine kinase-MM were transferred to 24-well culture plates and allowed to continue to grow for 3 to 5 days. Culture supernates were then re-examined by the enzyme inhibition assay and the standard ELISA test. Each supernate was examined by ELISA for reactivity with human creatine kinase-MM and in a separate test, human creatine kinase-BB.

(d) Isotype Screening

Each anti-human creatine kinase-MM antibody was scored for heavy chain class (isotype). Samples of each supernate were placed into each of 8 microtiter wells coated with human creatine kinase-MM (the eight wells in one column of a microtiter plate) and incubated 1 to 2 hours at RT. After washing the plate 5 times with Wash Buffer, diluted rabbit antiserum specific for each of the rat heavy chain classes were added to one of the eight wells. Separate wells were used for μ, γ1, γ2a, γ2b, γ2c, and α heavy chain classes. After 1 to 2 hours incubation the plates were washed 5 times with Wash Buffer. Horseradish peroxidase-conjugated goat anti-rabbit IgG (HRP-GAR) was then added to each well. After 1 to 2 hours incubation at room temperature, the plates were again washed 5 times with Wash Buffer. Substrate Buffer was then added and the plate was then incubated 10 to 30 minutes. Positive wells were scored by the presence of color (≧5 times background).

Cloning

The cloning process involves multiple steps of cultivating to propagate the selected hybridomas and screening to eliminate undesired hybridomas. Undesired hybridomas are those which secrete antibodies which are undesirable. For example, hybridomas that do not secrete antibodies or secrete antibodies that have cross-reactivity with the B-subunit of creatine kinase or are of the isotype which are difficult to work with are considered undesirable based on the objectives of the present invention.

After the fusing process is completed, each of the wells containing hybridomas are tested using the ELISA binding assay and the enzyme inhibition assay to identify those wells containing hybridomas producing antibodies which are specific to creatine kinase-MM.

These hybridomas are propagated as follows. The contents of each well identified as positive is transferred from the well to a tissue culture dish. The dish contains a first layer of agarose. A dilution of the contents of a single well is mixed with agarose and cast as a separate layer on the first layer of agarose. This second layer has a semi-solid consistency about that of gelatin at room temperature. It's designed to promote the growth of every hybridoma capable of growing and preventing mixing of cells due to convection or agitation. After a period of incubation, a third layer of agarose containing rabbit anti-rat-Fab antibody is coated above the second layer. The latter antibodies derived from rabbits will bind with any rat antibody. The anti-Fab antibody diffuses out of the third layer into the second layer and forms a precipitate around colonies growing in the second layer which produce antibodies of any type. To the eye, such precipitate looks like a halo around the colonies. Any colony growing in the second layer which makes an antibody of any type will produce this halo effect. Every hybridoma within the halo are sister cells and are expected to be making the same type of antibody.

Specifically herein, the procedure described generally above was carried out as follows. Two ml of 0.6% agarose in HT medium (HAT medium without aminopterin) was placed into each well of four-well (60 mm) culture plates. This base layer was refrigerated to allow it to cool and harden while the hybridoma cells were being prepared. Each cell line to be propagated was cultivated in a 24-well culture plate until it was growing vigorously. Serial dilutions of each cell line were prepared (in HT medium) and 0.5 ml of each suspension was mixed with 0.5 ml 1.2% agarose in HT-medium and quickly poured over a pre-cooled base layer. The cell layer was then cooled in a refrigerator to allow the agarose to become semi-solid.

The cells were then cultured for 6 to 10 days under standard conditions until macroscopic colonies were visible. A third agarose layer containing 0.6% agarose and 10% rabbit anti-rat (or mouse) Fab antiserum in HT-medium was then added to each well and allowed to cool. Typically, colonies secreting antibody had immunoprecititin "haloes" around them that were visible within 24 hours. Colonies secreting antibody were plucked with drawn glass pipets and transferred to 96 well microtiter plates. After 3 to 5 days of further growth the supernates were examined for anti-human creatine kinase-MM activity as described above.

At this point we have identified a series of colonies which are growing antibodies. The antibody type and the specific activity is not known. So when each are transferred to a microtiter well, they are cultured and allowed to grow for a while. Then the supernate fluid from each culture well is tested using ELISA and the inhibition assay to identify the antibodies which are specific to creatine kinase-MM. Those wells identified as positive are transferred to 24-well microtiter plates.

Hybridomas which secrete antibodies that cross-react with the B-subunit of creatine kinase can desirably be screened out at this point.

It is also desirable to eliminate those hybridomas secreting antibodies which are of the isotypes which are difficult to work with.

As a result of the foregoing multiple steps of cloning, screening, sub-cloning, screening, sub-cloning, 32 hybridomas were identified as secreting antibodies having the desired isotype, specificity and binding to and/or inhibition of creatine kinase-MM. The monoclonal antibodies secreted by each of the identified hybridomas were tested using ELISA binding and the inhibition assays to determine the degree to which they bind and/or inhibit the enzymatic activity of creatine kinase-MM and creatine kinase-MB.

The inhibition titer of the antibodies secreted by each of 32 different hybridomas was determined. The inhibition titer is defined for the purpose of this case as the minimum volume of an antibody containing supernate, secreted by a particular hybridoma, required to produce maximum possible inhibition, by that supernate, of the catalytic activity of creatine kinase-MM.

The inhibition titer was determined as follows for each hybridoma and its antibody containing supernate. The supernate is subjected to a series of dilution. The inhibition capability of each dilution is determined using the inhibition assay described hereinbefore in the screening section. An inhibition versus dilution curve was then plotted for the series. From this curve the maximum inhibition achieved and the minimum volume of supernate required to achieve that inhibition is observed and recorded. In the inhibition assay of the serial dilutions of each hybridoma secretion, no single hybridoma secreted a monoclonal antibody capable of inhibiting the catalytic activity of creatine kinase-MM sufficiently to allow an assay of creatine kinase-MB. In addition, it was learned that each secreted antibody containing supernate has a characteristic maximum degree of inhibition.

Next, the monoclonal antibodies secreted by the different hybridomas were tested as binary blends to determine whether such blends exhibited the degree of inhibition that would allow for a precise and accurate assay of creatine kinase-MB. Every possible combination, taken two at a time, of 33 different antibodies was tested. This represented 992 different combinations. Each different antibody was included in the blend at its individual inhibition titer level. Again, the conclusion was reached that no binary combination of monoclonal antibodies would provide the necessary inhibition of creatine kinase-MM that would allow for a precise and accurate assay of creatine kinase-MB.

Next, ternary blends were considered. Initially this meant assaying every possible combination of three different antibodies which were being secreted by the 32 different hybridomas. This represented about 4,960 different ternary combinations. This, of course, represented a formidable task.

Each ternary blend was tested for the maximum level of creatine kinase-MM activity inhibition as before. Again, each such blend included the different antibodies at their individual inhibition titer level. From those inhibition tests the following ternary blend was identified. The numerical designation of each hybridoma and its related antibody is based on internal bookkeeping and identification methods.

TABLE I

Properties of Monoclonal Antibodies Secreted by Hybridomas Formed by fusing SP2/0-Ag14 Mouse Myeloma Cells with Sprague-Dawley Rat Spleen Cells

| Monoclonal Antibody Name | Hybridoma 14.5 ATCC No. Filed May, 1987 CKMM 14.5 | Hybridoma 14.15 ATCC No. Filed May, 1987 CKMM 14.15 | Hybridoma 14.52 ATCC No. Filed May, 1987 CKMM 14.52 |
|---|---|---|---|
| Isotype (Heavy Chain Class & Light Chain Class) | IgA,K | IgG2a,K | IgG1,K |
| Inhibition of CKMM | 60 ± 5 | 90 ± 5 | 90 ± 5 |
| Inhibition of CKMB | 0 | 40 ± 5 | 40 ± 5 |
| Relative Binding CKMM and CKMB | CKMM only CKMB = 0 | CKMM = CKMB | CKMM > CKMB |

Table I identifies a ternary blend of three different monoclonal antibodies secreted from three different hybridomas. It is necessary to establish the relative amount of each antibody in the ternary blend needed to inhibit at least 99.5 percent of the creatine kinase-MM activity. The number or mass of antibodies in each supernate secreted by a particular hybridoma is not easily determined. However, the inhibition activity of a specified volume of the supernate can be readily determined. Thus, for the purpose of the present invention inhibition units (inh) are used to define the amount of each antibody required. One inhibition unit is defined as that volume of the original antibody containing supernate required to produce 50 percent of the characteristic level of inhibition of that antibody against a solution containing 2,000 I.U./liter of human creatine kinase-MM in the enzyme inhibition assay described previously.

More specifically, 25 μl of each dilution of a set of serial dilutions of the antibody containing supernate in PBS is mixed in a microtiter well with 25 μl of 4,000 u/L creatine kinase-MM in 0.1M Bis-Tris buffer pH 7.0. After thorough mixing, 150 μl of creatine kinase-NAC is added. The enzyme activity is assessed on a MCC 340 microplate reader (Titertek) modified for enzyme rate assays. That dilution containing a specified volume of antibody containing supernate, that produces 50 percent of its characteristic level of inhibition is one inh per specified volume of supernate in that dilution. The number of inhibition units in the undiluted supernate is obtained by dividing the volume of supernate containing one inhibition unit into the total volume of the undiluted supernate.

As an example, creatine kinase-MM 14.15 characteristically inhibits creatine kinase-MM activity 90 percent. Serial dilutions of creatine kinase-MM 14.15 each inhibit a 2,000 I.U./L challenge of creatine kinase-MM 90 percent until all inhibitory activity is diluted out (FIG. 1). The particular dilution at which 50 percent of the maximum inhibition for creatine kinase-MM 14.15 is produced (45%) is 1/256.

In FIG. 1, each dilution on the X axis represents the same volume, i.e. 10 ml. Thus 1.0, ½ ... 1/256 all represent the same overall volume. However, each dilution contains a different volume of the antibody containing supernate. At the X-Y intercept the volume is all concentrated supernate. In the dilutions ½ ... 1/256, represent the volume of the original supernate in a designated dilution.

The total inhibitory activity of a ternary blend of this invention must be sufficient to maximally inhibit at least 99.5 percent of the anticipated levels of creatine kinase-MM in a sample. These conditions can be met by mixing sufficient volumes of each antibody containing supernates to make the blend contain at least two inhibition units of each antibody.

Demonstration That Defined Blend of Monoclonal Antibodies Can be Used to Measure Creatine Kinase-MB The blend was used to assay creatine kinase-MB. Separate portions of the blend were incubated with a series of aqueous fluids having a known creatine kinase-MB and creatine kinase-MM activity. The assay was carried out using the enzyme inhibition assay described under the heading "Screening" herein. These assays showed that the ternary blend inhibited the enzyme activity of creatine kinase-MM at least 99.5 percent and creatine kinase-MB 40 percent.

Samples containing creatine kinase-MB at known levels (0-80 μ/L) in PBS with 1% BSA were assayed for creatine kinase activity under several conditions. One set (O) was assayed in the absence of the antibody blend. It defined the line for 100 percent of creatine kinase-MB activity. The second set (Δ) contained identical creatine kinase-MB samples in the presence of the antibody blend. It defines the measureable creatine kinase-MB activity in the presence of the antibody (58 percent of the total). The third set (□) contained creatine kinase-MB in the presence of a ternary antibody blend and 200 u/L creatine kinase-MM. The fourth (▽) contained creatine kinase-MB in the presence of the antibody blend and 2000 u/L creatine kinase-MM. These samples illustrate that creatine kinase-MB levels can be readily and accurately assessed in the presence of significant levels of creatine kinase-MM although some bias (6 u/L) is present in samples containing unusually high (2000 u/L) creatine kinase-MM levels.

All assays were performed in microtiter wells containing 50 μl of the samples plus 150 μl creatine kinase-NAC substrate scored on a Titertek MCC340 Microplate reader adapted for kinetic analysis at room temperature.

The results of the above assay are described in FIG. 1.

Curve 1, having the legend O represents the measurement of creatine kinase-MB in the absence of the ternary blend of antibodies. Curve 2, (Δ) represents the measurement of creatine kinase-MB in the presence of the blend. Curve 3 (□) represents the measurement of creatine kinase-MB in the presence of the blend and 200 units of creatine kinase-MM. Curve 4 (▽) represents the measurement of creatine kinase-MB in the presence of the blend and 2000 units of creatine kinase-MM.

This Curve 1 is a straight line showing the actual activity for a known series of creatine kinase-MB enzyme model solutions. The $Y_1$ intercept of Curve 1, passes ideally through zero on both the X and Y axes. Its slope $M_1$ is 1.0. Its correlation coefficient of linear regression $R_1$ is also 1.0.

Curve 2 is also a straight line having a $Y_0$ of $-1.2$; $M_0$ equals 0.58 and $R_0$ equals 0.998. In Curve 3, $Y_{200}$ equals $-0.65$; $M_{200}$ equals 0.575 and $R_{200}$ equals 0.999. In Curve 4 $Y_{2000}$ equals 6; $M_{2000}$ equals 0.583 and $R_{2000}$ equals 0.999.

A comparison of the data pictorialized in these curves shows that in the presence of a ternary blend of this invention, about 42% of the creatine kinase-MB is inhibited. This level of inhibition occurs in the presence of up to as much as 2000 units of creatine kinase-MM. This level of inhibition occurs with up 80 units of creation kinase-MB included in the model creatine kinase-MB solutions. This means that in the case of (a) Curve 4 ($6/2000 \times 100 = 0.3\%$) 99.7 percent of the creatine kinase-MM activity was inhibited and (b) Curve 3 ($-0.65/200 \times 100$) essentially all of the creatine kinase-MM activity was inhibited.

The above experiment shows that the ternary blend of monoclonal antibodies of the invention can be used to provide a precise and accurate measure of creatine kinase-MB in biological fluids.

It is recognized that the different antibodies secreted by the hybridoma described herein can be used as immunogens in selected animals to create antibodies which are species of the antibodies provided by the present invention. Such species are considered to be within the scope of the present invention.

The invention has been described in detail with particular reference to preferred embodiments thereof, but it will be understood that variations and modifications can be effected within the spirit and scope of the invention.

We claim:

1. A blend of monoclonal antibodies comprising:
    (a) a first monoclonal antibody that
        (i) inhibits the activity of creatine kinase-MM 55 to 65 percent;
        (ii) is a non-inhibitor of the catalytic activity of creatine kinase-MB;
        (iii) binds creatine kinase-MM and fails to bind creatine kinase-MB; and
        (iv) is secreted by a hybridoma having the designation 14.5 and an ATCC Deposit Number HB9420;
    (b) a second monoclonal antibody that
        (i) inhibits the catalytic activity of creatine kinase-MM 85 to 95 percent;
        (ii) inhibits the catalytic activity of creatine kinase-MB 35 to 45 percent;
        (iii) binds creatine kinase-MM and creatine kinase-MB equally; and
        (iv) is secreted by a hydridoma having the designation 14.15 and an ATCC Deposit Number HB9419; and
    (c) a third monoclonal antibody that (i) inhibits the catalytic activity of creatine kinase-MM 85 to 95 percent;
(ii) inhibits the catalytic activity of creatine kinase-MB 35 to 45 percent;
(iii) has greater binding strength to creatine kinase-MM than to creatine kinase-MB; and
(iv) is secreted by a hybridoma having the designation 14.52 and an ATCC Deposit Number HB9421.

2. The blend of claim 1 wherein each antibody is present in a sufficient amount to provide at least two inhibition units of each antibody.

3. An analytical method for determining the enzymatic activity of Creatine Kinase-MB in an aqueous biological sample, which comprises the steps of:
(A) incubating the sample with a blend of monoclonal antibodies that inhibits the enzymatic activity of the M-subunit of creatine kinase-MM or Creatine Kinase-MB at least 99.5% and is a non-inhibitor of the enzymatic activity of the B-subunit of creatine kinase-MB and creatine kinase-BB; wherein the blend of monoclonal antibodies comprises:
 (i) a first monoclonal antibody that
  (1) inhibits the activity of creatine kinase-MM 55 to 65 percent;
  (2) is a non-inhibitor of the catalytic activity of creatine kinase-MB;
  (3) binds creatine kinase-MM and fails to bind creatine kinase-MB; and
  (4) is secreted by a hybridoma having the designation 14.5 and an ATCC Deposit Number HB9420;
 (ii) a second monoclonal antibody that
  (1) inhibits the catalytic activity of creatine kinase-MM 85 to 95 percent;
  (2) inhibits the catalytic activity of creatine kinase-MB 35 to 45 percent;
  (3) binds creatine kinase-MM and creatine kinase-MB equally; and
  (4) is secreted by a hybridoma having the designation 14.15 and an ATCC Deposit Number HB9419; and
 (iii) a third monoclonal antibody that
  (1) inhibits the catalytic activity of creatine kinase-MM 85 to 95 percent;
  (2) inhibits the catalytic activity of creatine kinase-MB 35 to 45 percent;
  (3) has greater binding strength to creatine kinase-MM than to creatine kinase-MB; and
  (4) is secreted by a hybridoma having the designation 14.52 and an ATCC Deposit Number HB9421; and
(B) determining the enzymatic activity of the creatine kinase B-subunit.

4. A hybridoma having the designation 14.15 and an ATCC Deposit Number HB9419.

5. A monoclonal activity antibody that inhibits the catalytic activity of
(a) creatine kinase-MM from 85 to 95 percent;
(b) creatine kinase-MB from 35 to 45 percent;
(c) that binds creatine kinase-MB and creatine kinase equally; and
(d) that is secreted by a hybridoma having the designation 14.15 and an ATCC Deposit Number HB9419.

6. A hybridoma having the designation 14.5 and an ATCC Deposit Number HB9420.

7. A monoclonal antibody that
(a) inhibits the catalytic activity of creatine kinase-MM from 55 to 65 percent;
(b) is a non-inhibitor of the catalytic activity of creatine kinase-MB;
(c) binds creatine kinase-MM and does not bind creatine kinase-MB; and
(d) is secreted by a hybridoma having the designation 14.5 and an ATCC Deposit Number HB9420.

8. A hybridoma having the designation 14.52 and an ATCC Deposit Number HB9421.

9. A monoclonal antibody which
(a) inhibits the catalytic activities of creatine kinase-MM from 85 to 95 percent;
(b) inhibits the catalytic activities of creatine kinase-MB from 35 to 45 percent; and
(c) has greater binding strength to creatine kinase-MM than to creatine kinase-MB; and
(d) is secreted by a hybridoma having the designation 14.52 and an ATCC Deposit Number HB9421.

* * * * *